United States Patent
Chamney et al.

(10) Patent No.: US 10,195,328 B2
(45) Date of Patent: Feb. 5, 2019

(54) CALIBRATION OF A BODY PARAMETER FOR MONITORING DIALYSIS

(71) Applicant: Fresenius Medical Care Deutschland GmbH, Bad Homburg (DE)

(72) Inventors: Paul Chamney, Herts (GB); Ulrich Moissl, Karben (DE); Peter Wabel, Darmstadt (DE); Sebastian Wieskotten, Erfelden (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 883 days.

(21) Appl. No.: 14/409,685

(22) PCT Filed: Jul. 18, 2013

(86) PCT No.: PCT/EP2013/002143
§ 371 (c)(1),
(2) Date: Dec. 19, 2014

(87) PCT Pub. No.: WO2014/012670
PCT Pub. Date: Jan. 23, 2014

(65) Prior Publication Data
US 2015/0320920 A1 Nov. 12, 2015

(30) Foreign Application Priority Data
Jul. 19, 2012 (EP) .................................... 12005286

(51) Int. Cl.
*A61B 5/1455* (2006.01)
*A61M 1/16* (2006.01)
(Continued)

(52) U.S. Cl.
CPC ......... *A61M 1/1603* (2014.02); *A61B 5/0537* (2013.01); *A61B 5/4875* (2013.01); *A61B 5/4881* (2013.01)

(58) Field of Classification Search
None
See application file for complete search history.

(56) References Cited

U.S. PATENT DOCUMENTS 6,442,411 B1 * 8/2002 Guthermann ...... A61B 5/14532
600/310

OTHER PUBLICATIONS

Titapicoolo et al. Relative Blood Volume Monitoring during hemodialysis in end stage renal disease patients. 2010 Annual International Conference of the IEEE Engineering in Medicine and Biology Society, Aug. 31, 2010, pp. 5282-5285.
(Continued)

*Primary Examiner* — Eric Winakur
*Assistant Examiner* — Marjan Fardanesh
(74) *Attorney, Agent, or Firm* — Jacobson Holman, PLLC.

(57) ABSTRACT

A method and an apparatus for detecting a change of the fluid status or determining the fluid status of an individual are disclosed. The method comprises the following steps: determining a change of the body parameter (ΔRBV) of the individual during a first treatment session (201); determining a first fluid status of the individual (202); calibrating the determined change of the body parameter (ΔRBV) based on the first fluid status (205); determining the change of the body parameter (ΔRBV) of the individual during at least one further treatment session (207); and deriving a fluid status or a change of fluid status individual from the change of the body parameter (ΔRBV) (208).

13 Claims, 9 Drawing Sheets

(51) Int. Cl.
*A61B 5/053* (2006.01)
*A61B 5/00* (2006.01)

(56) References Cited

OTHER PUBLICATIONS

Yashiro et al. Natur of the Filtration Coefficients of the Microvasculature in the Vicinity of Dry Weight in Hemodialysis Patienets—As a Marker of the Fluid status. Complex Medical Engineering (CME) 2012, Jul. 1, 2012, pp. 255-260.
Dasselaar et al. Effedct of High and Low Ultrafiltration Volume during Hemodialysis on Relative Blood Volume. ASAIO Journal, vol. 52, No. 2, Mar. 1, 2006, pp. 169-173.
Wizemann et al. The mortality risk of overhydration in haemodialysis patients. Nephrol Dial Transplant (2009), 24:1574-1579.
Kuhlmann et al. Bioimpedance, dry weight and blood pressure control: new methods and consequences. Current Opinion in Nephrology and Hypertension, 2005, 14:543-549.
Chamney et al. A new technique for establishing dry weight in hemodiaysis patients via whole body bioimpedance. Kidney International, 2002, 61:2250-2258.
Piccoli et al. A new method for monitoring body fluid variation by bioimpedance analysis: The RXc graph. Kidney International, 1994, 46:534-539.
Chen et al. Extracellular water/Intracellular water is a strong predictor of patient survival in incident peritoneal dialysis patients. Blood Purification, 2007, 25:260-66.
Chamney et al. A whole body model to distinguish excess fluid from the hydration of major body tissues.Am J. Clin Nutr 2007; 85:80-9.
Zhu et al. Adjustment of dry weight in hemodialysis patients using intradialytic continuous multifrequency bioimpedance of the calf. The International Journal of Artificial Organs, vol. 27, No. 2, 2004, pp. 104-109.
Zhu et al. A method for the estimation of hydration state during hemodialysis using a calf bioimpedance technique. Physiological Measurement, 29 (20080, S503-S516.
Machek etal. Guided optimization of fluid status in haemodialysis patients Nephrol Dial Transplant 920100 25: 538-544.
Sinha et al. Relative Plasma Volume Monitoring During Hemodialsysis Aids the Assessment of Dry Weight. Hypertension. 210; 55: 305-311.
Guyton et al. Textbook of Medical Physiology, $8^{th}$ edition.
Guyton et al. Textbook of Medical Physiology, $10^{th}$ edition.

* cited by examiner

CALIBRATION OF A BODY PARAMETER FOR MONITORING DIALYSIS

The present disclosure concerns the calibration of a body parameter to the fluid status of an individual. The calibrated body parameter can subsequently be used as an indicator for the fluid status of the patient.

BACKGROUND

Fluid status is an important issue in long-term dialysis patients and is related to clinical outcome. In fact, knowledge of a patient's fluid status is essential in efficiently managing hemo- as well as peritoneal-dialysis patients. Chronic fluid overload is associated with left ventricular hypertrophy, left ventricular dilatation, arterial hypertension, and eventually the development of congestive heart failure. High interdialytic weight gain on top of chronic fluid overload further increases the burden for the cardiovascular system. Recent studies have shown that fluid overload can even be linked to an increased mortality (Wizemann V. et al., "The mortality risk of overhydration in haemodialysis patients", Nephrol. Dial. Transplant 2009, 24:1574-1579). Management of the fluid status involves restriction of sodium intake and, to the extent possible and over time, attainment of a post-dialysis weight equal to the patient's dry weight or normohydration weight.

Normohydration weight is defined as the weight the patient would have with zero fluid overload. Fluid overload can be expressed as excess extracellular fluid volume (ECV). In order to have a comparative standard for a reference to body mass, body composition or total body water (TBW) is required.

In comparison, dry weight may be defined as the weight at which an individual is as close as possible to a normal fluid status without experiencing symptoms indicative of fluid overload or deficit. Clinically, dry weight is determined as the lowest weight a patient can tolerate without developing intra- or interdialytic symptoms of hypovolemia. This clinical assessment is hampered by the fact that some liters of fluid may accumulate in the body before an oedema becomes clinically evident and that it does not account for changes in lean body mass, fat mass or nutritional status over time. In addition, some patients may have symptoms on dialysis for heart problems that may not be related to fluid overload.

Therefore, normohydration and dry weight are closely linked with dry weight being slightly less than normohydration weight.

Several methods of determining the fluid status of an individual exist:

Isotope dilution methods are frequently recommended for fluid volume measurement (ECV or TBW), but they are clinically not feasible because of complexity and expense. Furthermore, these methods can determine the absolute quantities of ECV and TBW but cannot determine the amount of excess extracellular water (fluid overload) and thus no value for the normohydration weight.

Efforts have been made in the past to use the bioimpedance technology to facilitate the fluid reduction process. Cf., for example, Kuhlmann et al., "Bioimpedance, dry weight and blood pressure control: new methods and consequences", Current Opinion in Nephrology and Hypertension, 2005, 14:543-549, the disclosure of which is entirely incorporated by reference.

Several different bioimpedance approaches to determine the optimal fluid status have been published:

The normovolemic-hypervolemic slope method, cf., e.g. Chamney et al., "A new technique for establishing dry weight in hemodialysis patients via whole body bioimpedance", Kidney Int., 2002, 61:2250-2258, the disclosure of which is entirely incorporated by reference, applies whole body multi-frequency bioimpedance to assess pre-dialytic total body extracellular fluid volume and compares the extracellular fluid volume/body weight relation at hypervolemia with the standard value in normovolemic individuals.

The resistance-reactance graph method, cf., e.g. Piccoli et al., "A new method for monitoring body fluid variation by bioimpedance analysis: the RXc graph", Kidney Int., 1994, 46:534-539, the disclosure of which is entirely incorporated by reference, uses whole body single frequency bioimpedance for assessment of fluid status and nutritional status from height-adjusted resistance and reactance. The resulting resistance-reactance vector is set in relation to a distribution range in a normovolemic population. The difficulty of this method is that it does not provide absolute values of the fluid status—patients can only be compared to percentiles of a normal population.

Whole body bioimpedance spectroscopy (wBIS) is a noninvasive technique calculating the "whole body" extracellular fluid volume (wECV) and the whole body intracellular fluid volume (wICV) by measuring resistance and reactance over a range of alternating current frequencies (e.g. 50 to 250 frequencies from ca. 1 kHz to 1000 kHz). Ratios of wECV or wICV to total body water volume (TBW) or the ratio wECV/wICV are used to assess the fluid status of a patient, cf., e.g. Wei Chen et al., "Extracellular Water/Intracellular Water Is a Strong Predictor of Patient Survival in Incident Peritoneal Dialysis Patients", Blood Purif., 2007, 25:260-266, the disclosure of which is entirely incorporated by reference.

The newest and more sophisticated technique is a whole body bioimpedance spectroscopy with a physiological tissue model: wECV and wTBW are measured by whole body bioimpedance spectroscopy and additionally the fluid status and body composition are calculated. This is achieved by setting the measured patient in relation to a subject with a normal fluid status and the same body composition. Thus it relates back to the normohydrated properties of tissue. This physiologic tissue model is described in "A whole-body model to distinguish excess fluid from the hydration of major body tissues", Chamney P. W., Wabel P., Moissl U. M. et al., Am. J. Clin. Nutr., 2007, January, 85(1):80-9, the disclosure of which is entirely incorporated by reference. This method allows the patient specific prediction of the normal fluid status and the normal fluid status weight—the weight, the patient would have with a working kidney. This method also allows to determine the composition of the individual including adipose tissue mass (ATM or $M_{AT}$), lean tissue mass (LTM or $M_{LT}$) and extracellular water volume ECW.

An alternative method (see, for example, Zhu et al., "Adjustment of dry weight in hemodialysis patients using intradialytic continuous multifrequency bioimpedance of the calf", Int. J. Artif. Organs, 2004, 12:104-109 and Zhu et al., "A method for the estimation of hydration state during hemodialysis using a calf bioimpedance technique", Physiol. Meas., 2008: S503-S516, the disclosures of which are entirely incorporated by reference) uses segmental bioimpedance in the form of continuous intradialytic calf bioimpedance to record changes in calf extracellular volume during dialysis. Normohydration weight determined by this method is defined as the body weight at which calf extracellular volume is not further reduced despite ongoing ultrafiltration. Although this method is good for estimating normohydration of a patient, the technique requires the performance of bioimpedance measurements throughout a dialysis session. In fact, a prediction of the normohydration weight is not feasible at all. In addition, patient movement at the lower limb is limited during the dialysis session and measuring electrodes have to be kept in place until the session is finished.

Fluid management of individuals undergoing dialysis and/or ultrafiltration comprises three main steps: 1) the assessment of fluid status, 2) the optimisation of fluid status towards normohydration and 3) the maintenance of an "optimized" normohydration fluid status corresponding to the normohydration weight.

The above described methods cover the first step, and using a fluid reduction protocol as described in Petr Machek et. al.: "Guided optimization of fluid status in haemodialysis patients", Nephrol Dial Transplant (2010) 25: 538-544, which is incorporated by reference in its entirety provides a solution for the second step. Nevertheless, an urgent need exists to find a solution for maintaining the optimal fluid status.

This is particularly tricky, since one has to detect if an individual's weight alternates due to a change of fluid overload or due to a change in normohydration weight because of a change in bodycomposition (lean or fat mass).

Changes in normohydration weight can occur very quickly and may be overlooked in a lot of cases, leading to subsequent over- or underhydration over a longer period of time if the dialysis postweight, i.e. the weight after a dialysis, is not adjusted.

Therefore, either the fluid status and/or the normohydration weight should be updated regularly, at best in every treatment.

Unfortunately, the above described bioimpedance methods cannot be used in every treatment, but rather on a monthly basis or even just once every three months, in particular due to costs and/or to discomfort that these methods cause to the monitored individual.

Various other approaches to detect a change in the fluid status have been developed, such as blood volume monitoring, ultrasound assessment of inferior vena cava diameter and several biochemical parameters, such as brain or atrial natriuretic peptide.

In particular blood volume monitoring or plasma volume monitoring is believed to be a good indicator for detecting a change of fluid status or even to determine dry weight of an individual, cf., e.g. A. D. Sinha et al.: "Relative Plasma Volume Monitoring During Hemodialysis Aids the Assessment of Dry Weight", Hypertension. 2010; 55: 305-311, the disclosure of which is entirely incorporated by reference. Plasma volume monitoring assesses the balance between refilling and ultrafiltration rate in respect to the absolute plasma volume. Fluid overload is one of many factors influencing this relationship. Plasma is thereby directly linked to blood volume. Relative blood volume is a ratio of the blood volume at a certain moment compared to an earlier determined blood volume, e.g. at the beginning of a treatment session.

It has often been reported that flat relative blood volume curves are a sign of excessive fluid overload. According to Guyton, about ⅔ of fluid overload contribute to the interstitial space, and the remaining ⅓ contributes to the plasma volume, c.f. Guyton A. C. et al., "JE. Textbook of Medical Physiology", Philadelphia, W.B. Saunders, 2000, the disclosure of which is entirely incorporated by reference. Both effects result in a flatter relative blood volume curve: firstly, interstitial fluid overload provides a fluid reservoir that facilitates refilling from the interstitial to the vascular space. Secondly, a 1 L decrease in plasma volume will lead to a smaller relative change if the absolute plasma volume is higher.

None of these approaches, however, give an accurate estimate of the change of fluid status (overload/normohydration) due to the fact that they have not been proven to be practical or reliable in the determination in individual patients. Consequently, a majority of dialysis patients may be fluid overloaded or depleted without specific symptoms.

Therefore, there exists an urgent need to find an applicable parameter which can be determined cost-efficiently, easily and regularly without causing discomfort or even distress to the patient.

Furthermore, an urgent need for a determination of a change in fluid status and/or a fluid status and a treatment of an individual based on such a parameter exists, in particular to avoid unnoticed fluid overload or depletion in treated individuals. Put simply, it would be beneficial for the adequate fluid management of individuals to quantify fluid overload or even to be able to estimate dry weight and/or normohydration weight more reliably without causing discomfort to the individual than currently done in clinical practice.

SUMMARY

The above-mentioned deficiencies in the art are addressed by the various embodiments of the present invention.

In one embodiment, the present disclosure relates to a method for calibrating a body parameter of an individual comprising the steps of determining a change of the body parameter of the individual during a first treatment session, determining a first fluid status of the individual, and calibrating the determined change of the body parameter based on the first fluid status.

In one embodiment, the present disclosure relates to a method for detecting a change of the fluid status or determining the fluid status of an individual comprising the steps of determining a change of the body parameter of the individual during a first treatment session, determining a first fluid status of the individual, calibrating the determined change of the body parameter based on the first fluid status, determining the change of the body parameter of the individual during at least one further treatment session and deriving a fluid status or a change of fluid status of the individual from the change of the body parameter.

In one embodiment, the present disclosure relates to a method of bringing an initially fluid overloaded individual into its normal fluid status comprising the steps of determining a change of the body parameter of the individual during a treatment session, determining a first fluid status of the individual, calibrating the determined change of the body parameter based on the first fluid status, determining the change of the body parameter of the individual during at least one further treatment session and deriving an updated fluid status of the individual from the change of the body parameter and reducing the fluid overload of the individual based on the derived fluid status.

In one embodiment, the present disclosure relates to a method for calibrating a body parameter of an individual further comprising the step of determining a second change of a body parameter and/or a second fluid status during a second treatment session, wherein the calibration of the change of the body parameter is based on the first and second change of a body parameter and/or fluid statuses.

In one embodiment, the present disclosure relates to a method for calibrating a body parameter of an individual, wherein the body parameter is relative blood volume and/or the concentration of hemoglobin in the blood.

In one embodiment, the present disclosure relates to a method for calibrating a body parameter of an individual, wherein the treatment session is a dialysis and/or ultrafiltration treatment session.

In one embodiment, the present disclosure relates to a method for calibrating a body parameter of an individual further comprising a step of approximating the change of the body parameter by a polynomial regression, preferably of first order.

In one embodiment, the present disclosure relates to a method for calibrating a body parameter of an individual, wherein calibrating comprises the determination of at least one constant C and/or a coefficient k of a polynomial.

In one embodiment, the present disclosure relates to a method for calibrating a body parameter of an individual, wherein the fluid status is determined by an assessment of a body composition of the individual.

In one embodiment, the present disclosure relates to a method for calibrating a body parameter of an individual, wherein the ultrafiltration rate is kept constant during the treatment sessions and/or among treatment sessions and/or the ultrafiltration volume is kept constant among treatment sessions.

In one embodiment, the present disclosure relates to a method for calibrating a body parameter of an individual further comprising normalizing the change of a body parameter by ultrafiltration volume, wherein calibrating the change of body parameter is based on this ratio.

In one embodiment, the present disclosure relates to a method for detecting a change of the fluid status or determining the fluid status of an individual further comprising the step of determining a second change of a body parameter and/or a second fluid status during a second treatment session, wherein the calibration of the change of the body parameter is based on the first and second change of a body parameter and/or fluid statuses.

In one embodiment, the present disclosure relates to a method for detecting a change of the fluid status or determining the fluid status of an individual, wherein the detected change of the fluid status and/or the determined fluid status is derived based on a polynomial regression, preferably of first order.

In one embodiment, the present disclosure relates to a method for determining a fluid status of an individual, wherein normohydration of the individual is reached, if the slope, in particular a slope of a polynomial regression of first order of the normalized change of the body parameter ($\Delta$RBV) reaches a certain threshold.

In one embodiment the present disclosure relates to detecting a change of a fluid status wherein a change of the relative blood volume during a succeeding treatment session is determined, wherein the step of detecting the change of the fluid status includes determining a first slope of the change of the relative blood volume during the further treatment session and determining a second slope of the change of the relative blood volume during the succeeding treatment session, wherein a difference between the first and the second slope is determined, and wherein a change of the fluid status is detected if the determined difference between the first and the second slope exceeds a predetermined threshold value.

The first and the second slope can be a linear slope or be determined by a non-linear fit.

The determined difference can be an absolute or a relative difference.

The predetermined threshold value may be between 5% and 15%, preferably between 8% and 12%, most preferably approximately 10%.

In one embodiment, the present disclosure relates to a method for detecting a change of the fluid status or determining the fluid status of an individual, wherein the change of fluid status triggers a new assessment of the body composition of an individual, preferably at the values used to determine the threshold.

In one embodiment, the present disclosure relates to a method of bringing an initially fluid overloaded individual into its normal fluid status further comprising a step of determining a second change of a body parameter and/or a second fluid status during a second treatment session, wherein the calibration of the change of the body parameter is based on the first and second change of a body parameter and/or fluid statuses.

In one embodiment, the present disclosure relates to an above method, wherein a first and/or second fluid status, an updated fluid status, a normal fluid status, a normohydration weight or any other data gained throughout a treatment session is transferred to a database via a data connection.

In one embodiment, the present disclosure relates to an above method, wherein the database is operated at a central server.

In one embodiment, the present disclosure relates to an above method, wherein the transferred data is processed such that statistics and/or conclusions for the treatment of the patient and/or a specific group of patients, in particular patients with comparable body parameters, may be derived.

In one embodiment, the present disclosure relates to an above method, wherein the fluid status and/or any other data gained throughout the treatment session is used to determine the dosage of a medicament, preferably of EPO, sodium and/or iron preparations.

In one embodiment, the present disclosure relates to an above method, wherein the fluid status is determined by bioimpedance spectroscopy of the individual.

In one embodiment, the present disclosure relates a medicament, preferably EPO, sodium and/or iron preparations, to be administered to a patient, wherein the dosage and/or the administration scheme of the medicament is determined based on the fluid status estimated according to a method of one of the above methods.

In one embodiment, the present disclosure relates to an apparatus, particularly with a memory and a digital signal processor, comprising a first determination unit configured to determine a change of a body parameter of the individual during a treatment session, a second determination unit to determine a first fluid status of the individual and a calibration unit to calibrate the determined change of the body parameter based on the first fluid status.

In one embodiment, the present disclosure relates to a computer program comprising instructions which, when being executed by a computer, cause the computer to execute an above method.

In one embodiment, the present disclosure relates to a computer-readable medium comprising instructions for the execution of an above method when the instructions are executed on a computer.

DETAILED DESCRIPTION

Figure 1:
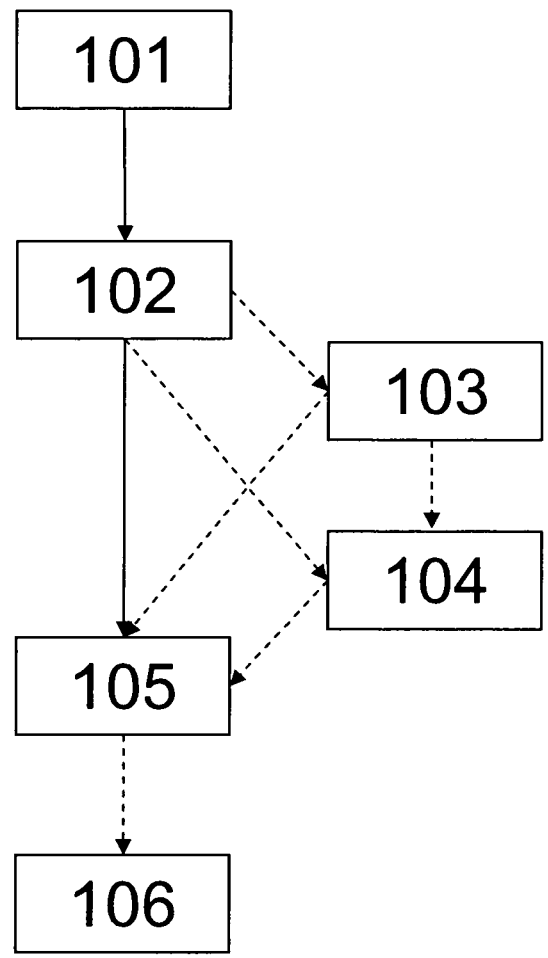
FIG. 1 depicts a flow diagram of a method of calibrating a body parameter in accordance with the teachings of the present invention.

As discussed above, in various of its embodiments, the present disclosure relates to the problem of calibrating a body parameter of an individual. The individual will typically undergo hemodialysis, peritoneal dialysis or other forms of dialysis as a result of renal failure.

Nevertheless, the methods and apparatus disclosed herein can also be used to assess the fluid status and/or reduce the fluid overload of individuals suffering from renal failure or other, e.g., cardiac failure (also cardio-renal syndrome), liver failure, and/or chronic kidney disease which has not yet led to the need for dialysis treatment. For example, knowledge of the fluid status or dry weight can be of value with cardiac failure individuals who are being treated with diuretics to reduce their fluid volume. As in dialysis, knowledge of the individual's fluid overload is of clinical significance in deciding how much diuretic to prescribe.

In addition, the methods and apparatus can be used in connection with assessing the fluid status of normal individuals, e.g., individuals participating in strenuous activity under high temperature and/or high humidity conditions, e.g. athletes. More generally, knowledge of an individual's fluid status may be beneficial in terms of controlling the intake of, for example, sodium in the patient's diet, e.g., the patient (either an ill subject or a normal subject) can monitor his or her water retention as a result of sodium intake by comparing his or her weight to a fluid status determined in accordance with the present disclosure. Having information regarding fluid status may be of particular interest to fitness enthusiasts and other persons particularly concerned with their state of health.

The methods and apparatus disclosed herein will typically be employed at various points in time so that the calibration of a body parameter will be current with changes in the individual's body composition, e.g., changes in the individual's fat and/or muscle content as a result of diet and/or exercise or the lack thereof.

In the sense of the present disclosure, a body parameter is defined as a parameter characterizing the physical state of an individual. Examples for body parameters are heart rate, respiratory rate, blood pressure, blood volume, relative blood volume, inferior vena cava diameter, several biochemical parameters, such as brain or arterial natriroatic peptide, body temperature, hemoglobin concentration, body weight, body volume, etc. and/or any combination thereof.

In the sense of the present disclosure, an individual is a human or an animal, in a healthy or ill condition.

In the sense of the present disclosure, a treatment session is defined as a unique, periodically or irregularly occurring treatment of an individual.

In the sense of the present disclosure, fluid status is the level of fluid in a body composition of an individual.

In the sense of the present disclosure, calibration is a comparison between measurements, one of known magnitude or correctness and another measurement, which magnitude or correctness is not known. The method of measurement with the known magnitude or correctness is called the standard. The second method of measurement is the calibrated method.

In the sense of the present disclosure, relative blood volume is the amount of blood volume in a second instance, compared to the amount of blood volume in a first instance, representing 100%. For example, a slope of relative blood volume may compare the blood volume during a dialysis treatment or ultrafiltration treatment session to the blood volume at the beginning of the treatment session. Relative blood volume is proportional to the relative plasma volume, such that one can be deduced from the other.

In the sense of the invention, a relative concentration of hemoglobin in the blood is the concentration of hemoglobin at a second instance compared to the concentration of haemoglobin in the blood at a first instance.

In the sense of the invention, normalising is the division or any other mathematical function of a parameter by a second parameter in order to limit or suppress the influence of the second parameter on the first parameter.

In the sense of the present disclosure, fluid overload means that the body of an individual comprises more fluid than in its normal fluid status corresponding to the normal fluid status weight, in particular a water excess or water intoxication.

In the sense of the present disclosure, dry weight is defined as the weight at which an individual is as close as possible to a normohydration status or weight without experiencing symptoms indicative of fluid overload or deficit, if the fluid status of the patient is such that the patient is above the hypervolemic symptomatic weight.

In the sense of the present disclosure, a normohydration weight is the gender specific weight of a healthy individual.

In the sense of the present disclosure, reducing the fluid overload is the loss of body fluid having an influence on the fluid status of a patient.

In the sense of the present disclosure, intradialytic is defined as during a treatment session.

In the sense of the present disclosure, interdialytic is defined as between treatment sessions.

In the sense of the present disclosure, body composition comprises relevant parameters for the composition of an individual's body, such as total body water, interstitial water, extra cellular water, lean tissue mass, adipose tissue mass, bone mass, muscle mass, etc.

In the sense of the present disclosure, slope4h is defined as the linear slope of the relative blood volume (RBV) over the full treatment normalized by the ultrafiltration rate (UFR).

According to the present disclosure, a body parameter of an individual is calibrated by the steps of determining a change of the body parameter of the body parameter ($\Delta$RBV) of the individual during a first treatment session (101), determining a first fluid status of the individual (102) and calibrating the determined change of the body parameter ($\Delta$RBV) based on the first fluid status (105).

By the means of the present invention, body parameters whose information on the physical condition of an individual is not completely known or understood can be calibrated individually for each individual based on the determined fluid status of the same. By this, the body parameter itself can serve in subsequent measurements as indicator for the physical condition of the individual, in particular for its fluid status.

The present invention therefore solves the problem that, even though body parameters could be used to find out the relative evolution of the fluid status, it was not possible to make a statement on the absolute value of the individual fluid status of an individual.

The fluid status of the individual may be determined before, after or during the treatment session and may comprise one or several determination points.

In a preferred embodiment a step of determining a second change of a body parameter ($\Delta$RBV) and/or a second fluid status during a second treatment session (103), is accomplished, wherein the calibration of the change of the body parameter ($\Delta$RBV) is based on the first and second change of a body parameter ($\Delta$RBV) and/or fluid statuses.

By calibrating the body parameter on a first and second fluid status, the calibration of the body parameter is even more exact. In particular for predicting a fluid level based on a change of the body parameter ($\Delta$RBV), the change in body parameter should be calibrated at two different fluid statuses. Based on these fluid levels, future fluid levels can be inter- or extrapolated.

In a further preferred embodiment the body parameter is relative blood volume (RBV), relative plasma volume and/or the concentration of hemoglobin in the blood.

As a particular advantage of the present invention body parameters which can be determined easily are used as the indicator for the physical condition of the patient, particularly his/her fluid status.

The above body parameters can be determined in a relatively simple manner. Measurement-techniques comprise photo-optical, electrical and chemical methods.

On the one hand the above body parameters are very convenient to measure, meaning that the examined individual does not have to suffer a limitation of its mobility and/or a physical distress and the sensors for measurement are cheap, reliable and robust.

On the other hand, the determination relies on equations which are easy to solve and give a robust result which is not volatile to small alterations of magnitude of the determined body parameter.

Another advantage of the present invention lies in the fact, that a correlation between a body parameter and the fluid status is introduced. This correlation permits to determine the fluid status without a genuine fluid status measurement and saves time and costs. Particularly, when the body parameter is a routinely and/or regularly checked parameter.

In a further preferred embodiment the change of the body parameter ($\Delta$RBV) during the treatment is approximated by a polynomial regression.

By approximating the curve of the body parameter change, a continuous evolution of the discretely determined points can be determined, the resulting curve can be smoothened and/or a value for the slope of the curve can be determined, also as an average over the whole curve.

In a further preferred embodiment the ultrafiltration rate is kept constant during the treatment session and/or between treatment sessions and/or the body parameter ($\Delta$RBV) is normalized by the ultrafiltration rate, wherein calibrating the change of body parameter ($\Delta$RBV) is based on this ratio.

By these techniques, an influence of different ultrafiltration rates on the determination of the body parameter can be prevented.

According to the present disclosure, a fluid status of an individual is determined wherein a dry weight of the individual is reached, if the slope in particular a slope of a polynomial regression of first order of the normalized change of the body parameter ($\Delta$RBV) reaches a certain threshold.

According to the present disclosure, a change of the fluid status is detected wherein the individual is treated during a treatment session succeeding the further treatment session and a change of the relative blood volume is determined during the succeeding treatment session. The step of detecting the change of the fluid status includes determining a first slope of the change of the relative blood volume during the further treatment session and determining a second slope of the change of the relative blood volume during the succeeding treatment session. A difference between the first and the second slope is determined, and a change of the fluid status is detected if the determined difference between the first and the second slope exceeds a predetermined threshold value.

The first and the second slope can be a linear slope or be determined by a non-linear fit.

The determined difference can be an absolute or a relative difference.

The predetermined threshold value may preferably be between 5% and 15%, more preferably between 8% and 12%, and most preferably approximately 10%.

In accordance with the teachings of the present invention, a reliable and simply to determine criterion is defined in order to determine the change of the fluid status.

Calibrating a body parameter of an individual is preferably based on a method as illustrated in FIG. 1. Merely by way of example, the calibration of a body parameter according to the present invention is demonstrated with respect to the relative blood volume (RBV) with the individual being a human patient being treated by ultrafiltration and/or dialysis. Nevertheless, as indicated above, the inventive methods can be applied to other body parameters and other forms of treatments.

In a first step of calibrating relative blood volume a change of the relative blood volume of the patient during a dialysis treatment session is determined (101). In a further step, which can be performed before, during or after the determination of the change of relative blood volume and thus before or after the dialysis treatment session, a first fluid status of the patient is determined (102). This is preferably performed by one of the methods described in the background section of the present patent application.

Preferably, the fluid status is determined by bioimpedance spectroscopy, even more preferably by a body composition monitoring with a Body Composition Monitor of Fresenius Medical Care®. In a another step of the inventive method, the determined change of the relative blood volume is calibrated based on the first fluid status (105). This means that a certain fluid status of the patient is assigned to a certain change of the relative blood volume (RBV), which is preferably represented by the slope of the timely evolution of the relative blood volume during a dialysis treatment session.

Figure 2:
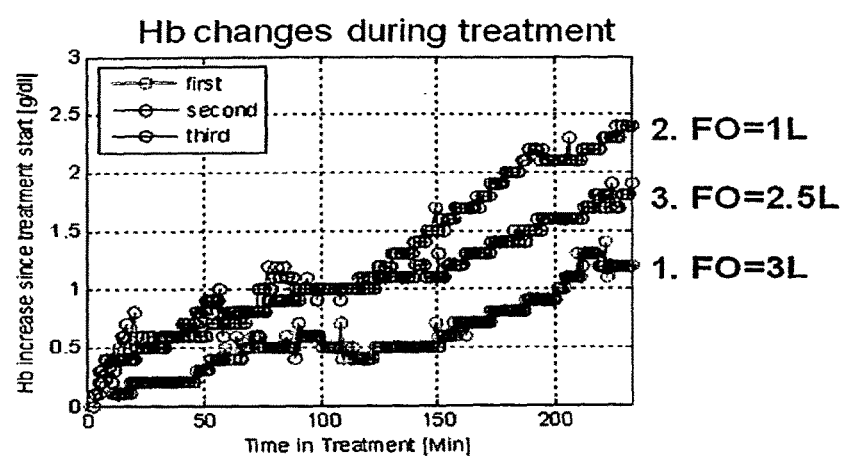
FIG. 2 depicts different intradialytic hemoglobin increase for one patient.

FIG. 2 represents an intradialytic hemoglobin (Hb) increase in one patient at different fluid overload (FO) levels. The time span between the measurements was one month and the ultrafiltration volume (UFV) was kept constant at 3.3 L in all three ultrafiltration treatments. At a high fluid overload (FO) of 3 L, the slope of the hemoglobin (Hb)

concentration curve is flatter than at a fluid overload of 1 L. Hemoglobin (Hb) was determined by a blood volume monitoring (BVM), therefore it reflects an "inverse" relative blood volume (RBV).

By means of the invention, to every timely evolution of the relative blood volume (RBV) and/or the concentration of hemoglobin, i.e. a change of the body parameter, a fluid status can be assigned. For the changes of the relative blood volume with a flatter timely development, i.e. slope, one then knows that it represents a higher fluid overload whereas a steeper development of the change of relative blood volume ($\Delta$RBV) represents a lower fluid overload or fluid status.

In one preferred embodiment, the inventive method comprises a step of determining a second change of a body parameter ($\Delta$RBV) and/or a second fluid status during a second treatment session (103), wherein the calibration of the change of the body parameter ($\Delta$RBV) is based on the first and second change of a body parameter ($\Delta$RBV) and/or fluid statuses.

The calibration of the change of the relative blood volume ($\Delta$RBV) is then based on the first and second fluid status. This allows for a more exact calibration of the relative blood volume (RBV) since two determined volumes of the fluid status exist to verify the corresponding change of relative blood volume ($\Delta$RBV). Also, a calibration of a body parameter such as the change of relative blood volume ($\Delta$RBV). in at least two different treatment sessions at different fluid statuses allows for a deduction of the fluid status in a further determination of relative blood volume ($\Delta$RBV), which will be explained in more detail below.

In order to be able to draw a better comparison between the determined change of the relative blood volume ($\Delta$RBV) and the determined fluid status or statuses, the evolution of the change of the relative blood volume ($\Delta$RBV) is approximated by polynomial regression in a further step (104). In fact, a polynomial regression enhances the reproducibility of the determination of the change of the relative blood volume ($\Delta$RBV).

Both, the steps of the second determination as well as of the polynomial regression are optional which is represented by the dashed flashes in the figures.

Preferably, the ultrafiltration volume (UFV) and/or the ultrafiltration rate (UFR) is kept constant during the ultrafiltration or dialysis treatment session or between treatment sessions. This enhances the comparability of the results among the determinations of the change.

Another preferred embodiment to enhance the comparability is to normalize the change of the body volume parameter (RBV) by the ultra filtration volume and/or the other filtration rate applied (106). More preferably, slope4h defined as the linear slope of the relative blood volume (RBV) over the full treatment normalized by the ultrafiltration rate (UFR) is used. One way to accomplish normalization is to simply divide the determined change of relative blood volume ($\Delta$RBV) by the value of the ultrafiltration volume (UFV) and/or the ultra filtration rate (UFR), respectively. In fact, confidence intervals were found to be extraordinarily high for a normalized slope, e.g. slope4h.

Figure 3:
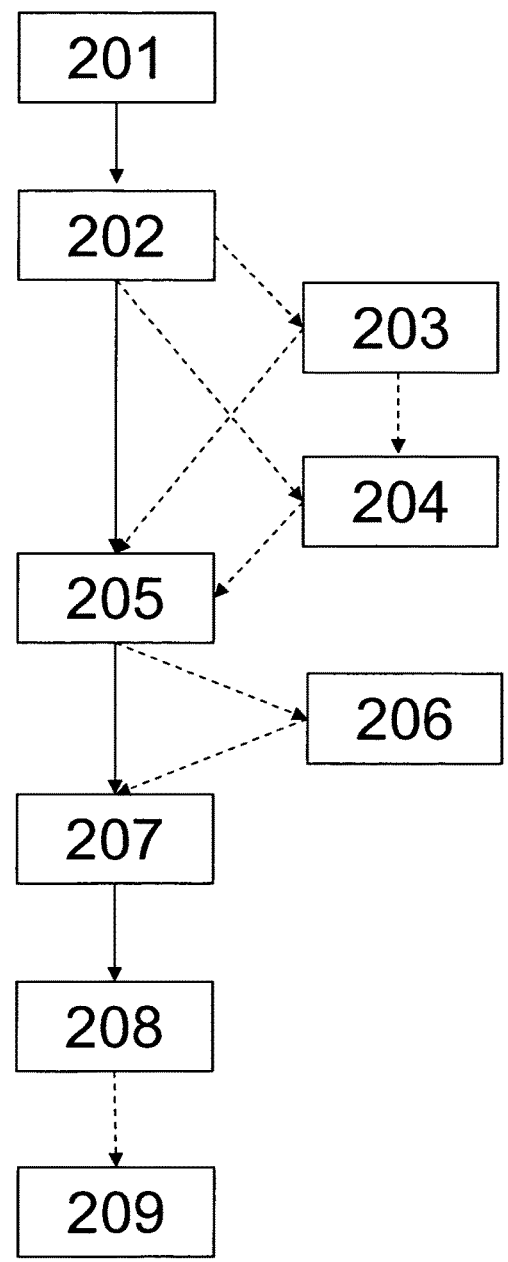
FIG. 3 depicts a flow diagram of a method for determining a fluid status or detecting a change of the fluid status in accordance with the teachings of the present invention.

In FIG. 3, a flow diagram for a determination of the fluid status and a detection of a change of the fluid status of an individual according to a method in accordance with the teachings of the present invention is described.

This method can be combined with the method of calibrating a body parameter as described in the foregoing.

In a first step of this method (201), a change of the relative blood volume ($\Delta$RBV) is determined during a first treatment session. In a further step, a first fluid status of the patient is determined (202). In a third step, the calibration of the determined change of the relative blood volume ($\Delta$RBV) based on the first fluid status is accomplished (205).

According to a preferred embodiment, in a further step a second change of a body parameter ($\Delta$RBV) and/or a second fluid status during a second treatment session (203) is determined, respectively. The calibration of the change of the body parameter ($\Delta$RBV) is subsequently based on the first and second change of a body parameter ($\Delta$RBV) and the first and second fluid statuses.

Furthermore according to preferred embodiments of this inventive method, the change of the relative blood volume ($\Delta$RBV) can be approximated by polynomial regression which can then preferably be used to determine the slope of the timely evolution of the change of relative blood volume ($\Delta$RBV) during a dialysis treatment session (204) and/or the change of the relative blood volume (206) can be normalized.

In yet another step, the change of the relative blood volume ($\Delta$RBV) is determined during at least one further treatment session (207). With this information at hand, the fluid status or a change of the fluid status can be derived from the change of the body parameter, here the relative blood volume ($\Delta$RBV) or the hemoglobin concentration, in a further step (208).

This can be achieved using the formalism described in the ANNEX.

According to this method, the calibrated change of relative blood volume ($\Delta$RBV) is used to deduce the fluid status or a change of the fluid status. A genuine measurement of the fluid status to detect a change, e.g. by bioimpedance spectroscopy, can be replaced. The relative blood volume (RBV) becomes therefore a marker for changes in the fluid status of a patient.

As mentioned above, this marker is not limited to the relative blood volume (RBV). For example, the above method may also be applied to the change of hemoglobin concentration in the blood of an individual.

In another preferred embodiment of this method, the detected change of fluid status serves as a trigger to induce an assessment of the body composition of an individual (209). By this, situations in which a patient becomes severely overhydrated or depleted without a weight change can be inhibited.

According to preferred embodiments, a trigger may be set as follows.

The individual is treated during a treatment session succeeding the further treatment session and a change of the relative blood volume is determined during the succeeding treatment session. The step of detecting the change of the fluid status includes determining a first slope of the change of the relative blood volume during the further treatment session and determining a second slope of the change of the relative blood volume during the succeeding treatment session. A difference between the first and the second slope is determined, and a change of the fluid status is detected if the determined difference between the first and the second slope exceeds a predetermined threshold value.

The predetermined threshold value may preferably be between 5% and 15%, more preferably between 8% and 12%, and most preferably approximately 10%. The thus detected change of the fluid status then serves as a trigger to induce to induce an assessment of the body composition of an individual (209).

By the determined change of the relative blood volume ($\Delta$RBV), in addition to having a marker for when the fluid status of a patient changes, the fluid overload can be directly deducted from the measured values: alternatively to deriving a change of the fluid status from the change of the body parameter in step (208), the actual value for the fluid overload (FO) may be derived.

In a simple way this may be performed by just knowing that the above mentioned slopes correspond to a discrete value for the fluid status of an individual.

Alternatively, continuous values for the fluid status may be derived from the change of the body parameter, here the change of the relative blood volume (ΔRBV) or hemoglobin concentration. This can be achieved by using the formalism described in the ANNEX.

One might, in a preferred embodiment of the inventive method, deduce a limit for the change of the relative blood volume (ΔRBV) where the dry weight of the patient is reached. Ultrafiltration can then be immediately reduced to a lower level to avoid intradialytic symptoms of the patient.

Figure 4:
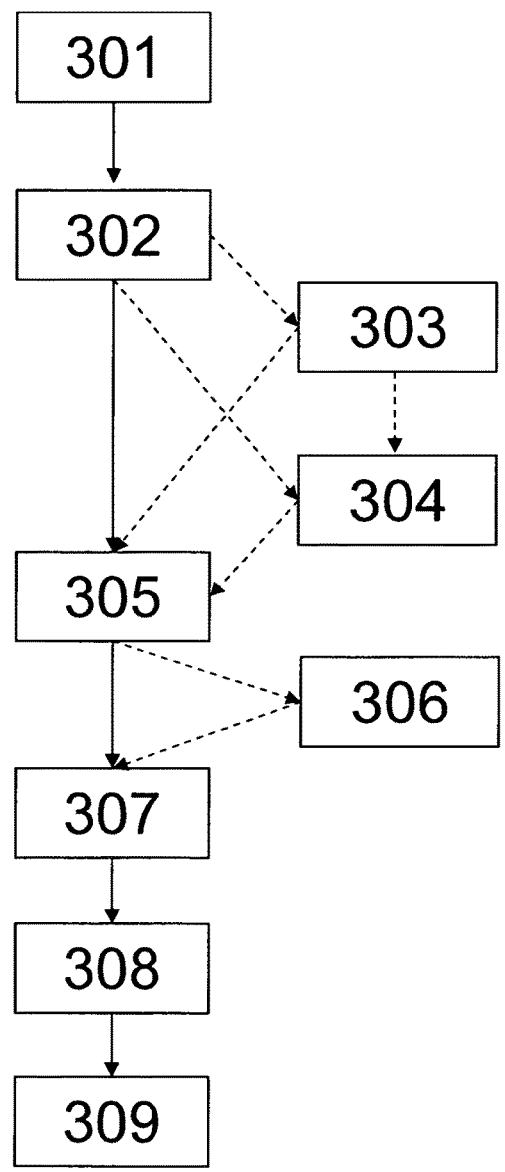
FIG. 4 depicts a method of bringing an initially fluid overloaded individual into its normal fluid status in accordance with the teachings of the present invention.

A further method in accordance with the teachings of the present invention is demonstrated in FIG. 4.

This method can be combined with the method of calibrating a body parameter and/or a method for detecting a change of the fluid status or determining a fluid status as described in the foregoing.

The further inventive method brings an initially fluid overloaded individual into its normal fluid status. Basically, this method uses the method to determine a fluid status or detect a change of the fluid status (steps 301 to 308) and then reduces the fluid overload of the patient based on the fluid status (309). By this, intra-dialytic symptoms can be prevented since, due to the knowledge of the fluid status of the patient, the ultrafiltration rate (UFR) or volume (UFV) can already be controlled before the beginning of the treatment session in order to avoid such symptoms. In a preferred embodiment, the fluid status can be predicted by the equations, presented in relation with the method to determine a fluid status described in the ANNEX.

The fluid status may also be controlled "online", since from the slope of the body parameter at the beginning of the treatment session, preferably the first 50 or 100 minutes, a fluid status which will be reached during the treatment session can be deduced.

Figure 5:
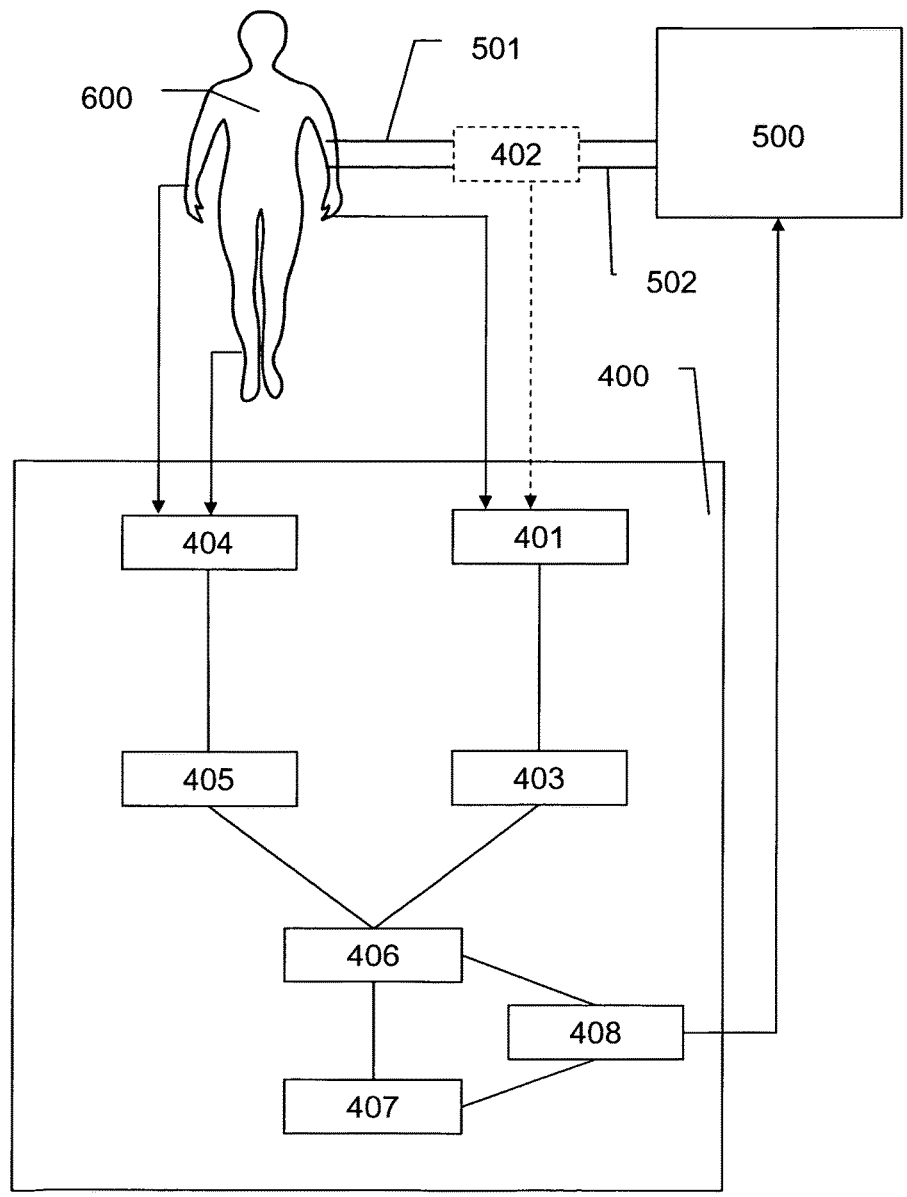
FIG. 5 depicts an apparatus for calibrating a body parameter of an individual in accordance with the teachings of the present invention.

FIG. 5 represents an apparatus (400) to accomplish the methods described above. In this figure, an individual, here a human patient, is dialyzed by a dialyzer 408. The blood of the patient is transported through the dialyzing lines (501, 502) to and from the dialyzer.

The apparatus (400) comprises a first determination unit (401) to determine a change of a body parameter, in this example the relative blood volume (ΔRBV) or hemoglobin concentration of the patient during a dialysis treatment session. The change of the body parameter may be determined with a sensor directly at the body of the patient or by a measuring unit (402) on samples of the blood flow of the blood lines (501, 502) of the dialyzer (500). Therefore, a determination does not imply a measurement on the body of the patient.

The acquired data is then preferably processed by a first processing unit (403) and provided to a calibration unit (406).

The fluid status of a patient is determined by a measuring unit (404), preferably by bioimpedance spectroscopy, in this example by whole body bioimpedance spectroscopy on the wrist and ankle of a patient. In a particularly preferred embodiment a BCM—Body Composition Monitor device of Fresenius Medical Care® is used to determine the body composition of the patient and to derive the fluid status from his/her body composition.

Preferably, this data is also processed by a second processing unit (405) and provided to the calibration unit (406). The calibration unit is adapted to perform the method of calibrating a body parameter of an individual according to the present invention.

In a preferred embodiment, the apparatus (400) further comprises a determination unit (407) to detect a change of the fluid status and/or to determine a fluid status. In a further preferred embodiment, the apparatus (400) comprises a control unit (408) to control the dialyzer (500), in particular the ultrafiltration rate (UFR) or the ultrafiltration volume (UFV) and therefore to control the reduction of the fluid overload by the dialyzer (500) based on the determined fluid status and/or the detected change of the fluid status, respectively.

The data in order to perform the control may be provided by the calibration unit and/or the determination unit as indicated by the connections in the schema of FIG. 5.

In a preferred embodiment, at a certain change of the fluid of the body parameter (e.g. relative blood volume (ΔRBV)) and therefore of the fluid status the control unit triggers an assessment of the body composition of the patient with the second measuring unit (404) or another unit (not represented).

The apparatus (400) is preferably an ordinary personal computer, a tablet PC or similar and all the units are preferably realized in just one processor and one memory (not illustrated).

ANNEX

The purpose of this ANNEX is to develop a relationship between blood volume and overhydration that could be exploited using measured variables that can be readily obtained during treatment, in particular during a dialysis and/or ultrafiltration treatment session. Consequently this allows several applications to be developed involving BVM and BCM. One of the key steps is to make use of the tissue hydration constants (body composition information) to obtain values of the extracellular water volume at normohydration $ECW_{Norm}$ and the blood volume at normohydration $BV_{Norm}$. This ANNEX covers all the details necessary to arrive at the following expressions which are the key link between BCM and BVM.

At any time during treatment the following relationship holds (parameters not introduced already will be introduced in this ANNEX):

$$\dot{R} \cdot BV_{Norm} + \dot{R} \cdot f_n(OH(0)) + Q_{UFR}(t) = [ECW_{Norm} + OH(0) - V_u(t) - RBV(t) \cdot (ECW_{Norm} + OH(0))] \cdot k_r$$

$\dot{R}$ being the time derivative of the blood volume or blood volume slope, $d(RBV)/dt$.

As will be explained further below, at t=0+ (immediately after the start of treatment) the overhydration may be determined as follows $$OH(0) = \frac{-1}{\lambda} \cdot \ln\left(\frac{Q_{ufr}(0^+) + \dot{R}(0^+) \cdot BV_{Norm}}{\dot{R}(0^+) \cdot \beta \cdot \delta V_{i\_Gel\_max}}\right) \forall\, OH \geq 0$$

$$OH(0) = \frac{-Q_{ufr}(0^+) - \dot{R} \cdot BV_{Norm}}{\dot{R} \cdot \alpha \cdot \beta} \forall\, OH < 0$$

Normal Values of ECW and BV at Zero Overhydration

Typical values of extracellular water, $ECW_{Norm}$, and blood volume, $BV_{Norm}$, and other parameters used in this ANNEX are provided by the references and by Table 1.

TABLE 1

Reference values to obtain $ECW_{Norm}$ and $BV_{Norm}$

| Variable | Description | Value | Source |
|---|---|---|---|
| $M_{WB}$ | Whole body weight | 73 kg | Ref 1 |
| $M_{fat}$ | Mass of fat (non-essential lipid) | 14.6 kg | Ref 1 |
| $H_{tw\_AT}$ | Total hydration of adipose tissue | 0.197 | Ref 2 |
| $K_{ar}$ | Adipose tissue residual mass fraction | 0.05 | Ref 2 |
| $M_{AT}$ | Mass of adipose tissue | 19.4 | Eq. 1 |
| $M_{LT}$ | Mass of lean tissue | 53.6 | Eq. 2 |
| $H_{ecw\_AT}$ | Hydration mass fraction of normally hydrated adipose tissue | 0.127 | Ref 2 |
| $H_{ecw\_LT}$ | Hydration mass fraction of normally hydrated adipose tissue | 0.266 | Ref 2 |
| $ECW_{Norm}$ | Normally hydrated extracellular water | 16.7 L | Eq. 3 |
| $BV_{Norm}$ | Normal blood volume | 5.6 L | Eq. 4 |

Background knowledge on the subject matter is disclosed in references Ref. 1, Ref. 2 and Ref. 3, the entire content of which is hereby incorporated by reference.

Ref 1: Chamney P W, Wabel P, Moissl U M et al. *A whole-body model to distinguish excess fluid from the hydration of major body tissues. Am J Clin Nutr* 2007; 85: 80-89

Ref 2: ICRP. *Basic anatomical and physiological data for use in radiological protection: reference values. ICRP Publication* 89. Ann ICRP 2002; 32:5-265.

Ref 3: Guyton A C. *Medical Textbook of Physiology*, 1991

$$M_{AT} = \frac{M_{Lipid}}{(1 - H_{tw\_AT} - K_{ar})} \qquad \text{Eq. 1}$$

$M_{Lipid}$ being the lipid mass.

$$M_{LT} = M_{WB} - M_{AT} \qquad \text{Eq. 2}$$

$$ECW_{Norm} = H_{ecw\_LT} \cdot LTM + H_{ecw\_AT} \cdot ATM \qquad \text{Eq. 3}$$

$$BV_{Norm} = 0.1 \cdot LTM + 0.01 \cdot ATM \qquad \text{Eq. 4}$$

Effects of Overhydration on ECW and BV

Figure 6:
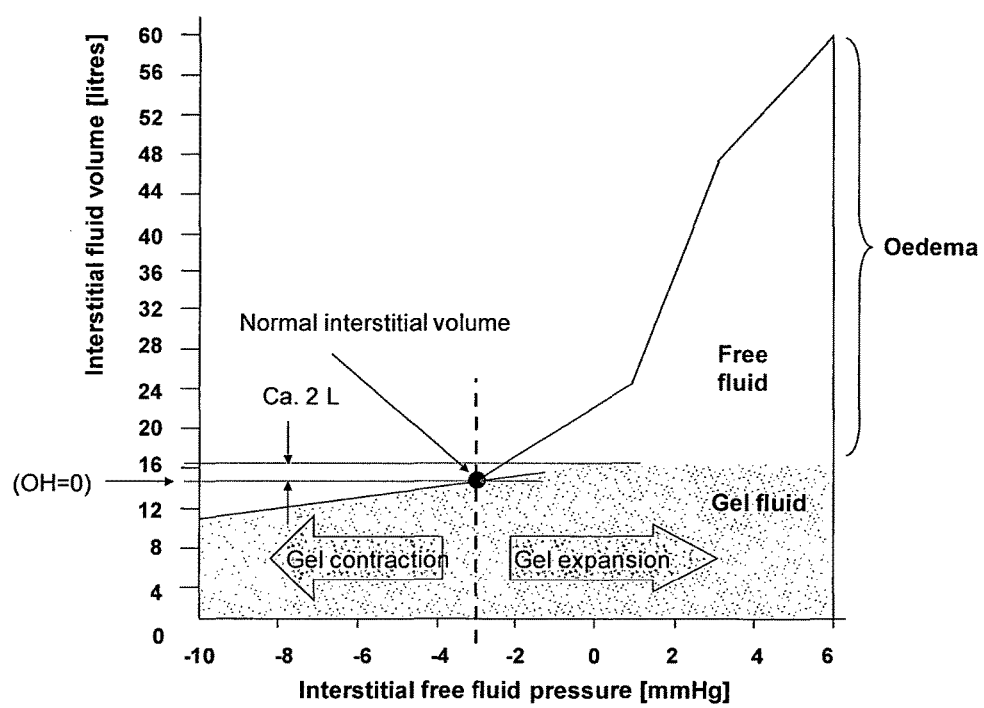
FIG. 6 depicts a relationship between interstitial pressure and interstitial fluid volume

The interstitial space has the well known relationship depicted in FIG. 6.

Adapted from Guyton (Ref 3). Note 2 L of gel expansion as subject becomes overhydrated.

Figure 7:
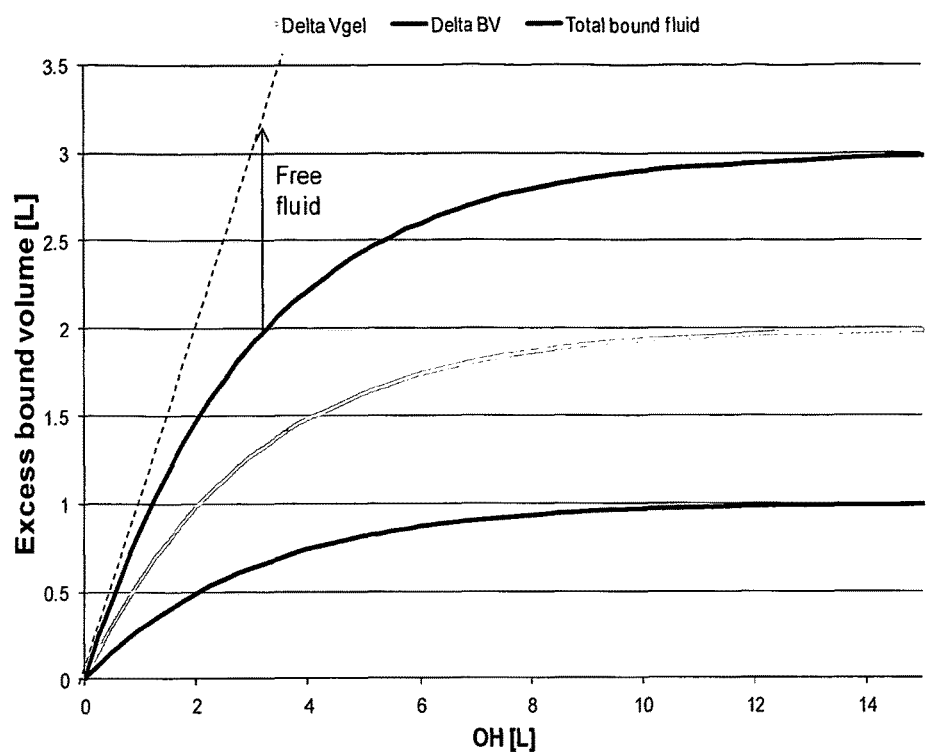
FIG. 7 depicts a dependency of bound fluid volumes in relation to overhydration

The excess bound volume in interstitial and blood volume compartments caused by overhydration is depicted in FIG. 7, the lower line indicating the portion of the bound overhydration associated with the blood volume, the middle line indicating the overhydration associated with the Gel compartment, and the upper line indicating the total bound fluid $OH_{bound}$.

The free fluid $OH_{free}$ is i the difference between the identity line corresponding to the total mass of the overhydration $OH_{total}$ and the total bound fluid $OH_{bound}$, ie.

$$OH_{total} = OH_{bound} + OH_{free}$$

Interstitial Volume Relationships

At zero overhydration, using reference data, the ratio of normal interstitial volume $V_{i\_Gel\_Norm}$ to normal extracellular water $ECW_{Norm}$ is:

$$\frac{V_{i\_Gel\_Norm}}{ECW_{Norm}} = \alpha = \frac{ECW_{Norm} - BV_{Norm}}{ECW_{Norm}} \qquad \text{Eq. 5}$$

$\alpha$ being a proportionality constant.

If reference values for $V_{i\_Gel\_Norm}$ and $ECW_{Norm}$ are substituted into Eq. 5, then $\alpha = 0.671$. $\alpha$ can be calculated from Eq. 5 substituting values from Eq. 3 and Eq. 4

Where negative overhydration occurs the interstitial volume is linearly dependent on the extracellular water volume ECW or overhydration OH, i.e.

$$V_{i\_Gel}(0) = \alpha \cdot ECW(0) = V_{i\_Gel\_Norm} + \alpha \cdot OH(0) \forall OH < 0 \qquad \text{Eq. 6}$$

$V_{i\_Gel}$ being the volume of the interstitial or Gel compartment and the index Norm indicating values at Normohydration The expansion of the interstitial space (the gel) as a subject becomes overhydrated could be approximated by a simple exponential function:

$$\delta V_{i\_Gel}(0) = \delta V_{i\_Gel\_max} \cdot (1 - e^{-\lambda \cdot OH(0)}) \forall OH(0) \geq 0 \qquad \text{Eq. 7}$$

$\lambda$ being a proportionality constant.

At zero overhydration the gradient of Eq. 7 must be equal to $\alpha$. In other words $$\frac{V_{i\_Gel\_Norm}}{ECW_{Norm}} = \alpha = \delta V_{i\_Gel\_max} \cdot \lambda \cdot e^{-\lambda \cdot OH(0)} \qquad \text{Eq. 8}$$

Thus $$\lambda = \frac{\alpha}{\delta V_{Gel\_max}} \qquad \text{Eq. 9}$$

$\delta V_{i\_Gel\_max}$ is 2 L for reference man. If $\delta V_{i\_Gel\_max}$ is assumed proportional to $ECW_{Norm}$ then $$\delta V_{i\_Gel_{max}} = \qquad \text{Eq. 10}$$
$$\frac{\delta_{i\_Gel_{max}\_ref}}{ECW_{Norm\_ref}} \cdot ECW_{Norm} = \frac{2}{16.7} \cdot ECW_{Norm} = 0.12 \cdot ECW_{Norm}$$

Relation of Blood Volume to Interstitial Volume

Under conditions of normal hydration (OH=0), the interstitial volume is approximately double the size of the blood volume. If this relationship is assumed to hold true for gel contraction during dehydration then from Eq. 6

$$BV(0) = \beta \cdot [V_{i\_Gel\_Norm} + \alpha \cdot OH(0)] = BV_{Norm} + \alpha \cdot \beta \cdot OH(0)$$
$$\forall OH(0) < 0 \qquad \text{Eq. 11}$$

Where $\beta$ is a constant of proportionality, typically 0.5. Note that the product $\alpha \cdot \beta = k_{Guy\_Norm}$. In the non-linear region of blood volume, occurring during overhydration (OH≥0), the blood volume is assumed to remain proportional to the volume of bound interstitial volume.

$$BV(0) = BV_{Norm} + \delta BV(0) = BV_{Norm} + \beta \cdot \delta V_{i\_Gel}(0) = \qquad \text{Eq. 12}$$
$$\beta \cdot \delta V_{i\_Gel\_max} \cdot (1 - e^{-\lambda \cdot OH(0)}) \forall OH(0) \geq 0$$

The index $\delta$ indicates a deviation of a value from the corresponding value at normohydration.

Modified Guyton relationship

Figure 8:
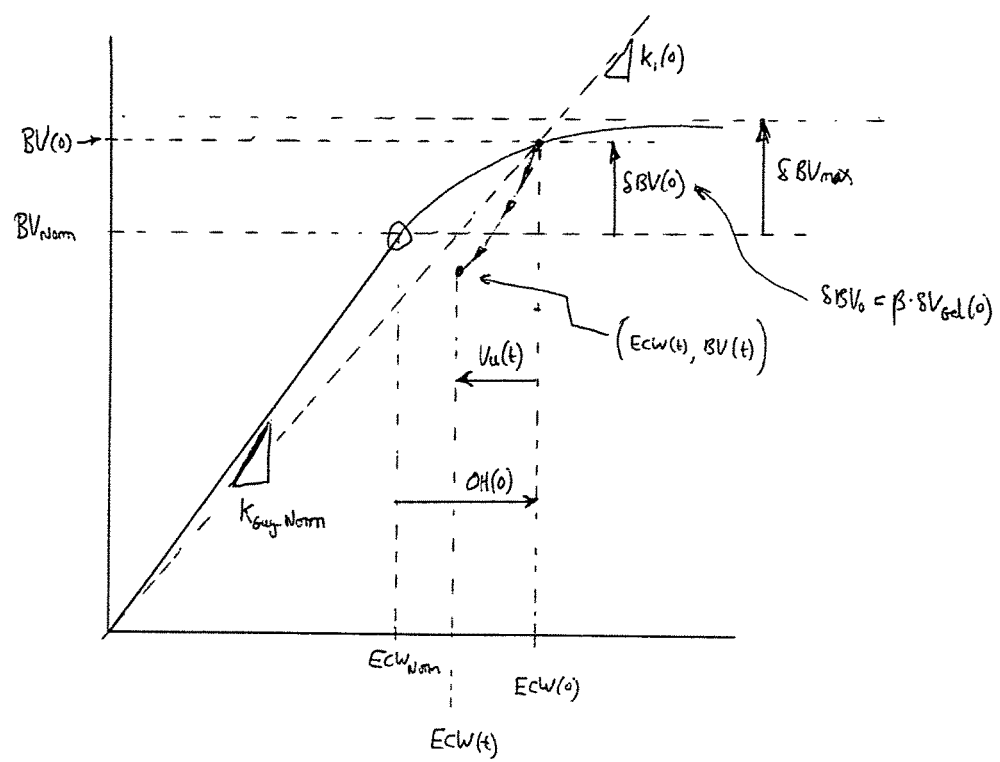
FIG. 8 depicts a dependency of blood volume BV in dependency of extracorporal water ECW

As $BV_{Norm}$ corresponds with $ECW_{Norm}$ and $ECW = ECW_{Norm} + OH$, the Guyton relationship can now be plotted via Eq. 11 and Eq. 12 as shown in FIG. 8. Initial conditions of ECW(0) and BV(0) are shown for later explanation.

FIG. 8 depicts the Guyton relationship. i.e. BV in relation to ECW

Let function $f_1$ be $$f_1(OH(0)) = \alpha \cdot \beta \cdot OH(0) \,\forall\, OH(0) < 0 \qquad \text{Eq. 13}$$

And let function $f_2$ be $$f_2(OH(0)) = \beta \cdot \delta V_{i\_Gel\_max} \cdot (1 - e^{-\lambda \cdot OH(0)}) \qquad \text{Eq. 14}$$

Thus Eq. 11 and Eq. 12 can be simplified to $$BV(0) = BV_{Norm} + f_1(OH(0)) \,\forall\, OH < 0 \qquad \text{Eq. 15}$$

$$BV(0) = BV_{Norm} + f_2(OH(0)) \,\forall\, OH(0) \geq 0 \qquad \text{Eq. 16}$$

Blood Volume Dynamics

The blood volume slope, $d(RBV)/dt$ or $\dot{R}$ is related to the difference between the refill rate, $Q_{refill}$ and ultrafiltration rate, $Q_{ufr}$ and the absolute blood volume $BV_0$ as $$\frac{d(RBV(t))}{dt} = \frac{Q_{refill}(t) - Q_{ufr}(t)}{BV_0} = \dot{R} \qquad \text{Eq. 17}$$

Making the assumption that the vascular refill rate, $Q_{refill}(t)$ is linearly proportional to the difference between the volume of the extracellular water ECW and the blood volume BV then $$Q_{refill}(t) = [ECW(t) - BV(t) \cdot k_1(0)] \cdot k_r \qquad \text{Eq. 18}$$

Where $k_r$ is a patient specific refill constant (units of Time$^{-1}$) to be optimized and $k_1(0)$ is a dimensionless scaling constant as indicated on FIG. 8. At initial conditions, $Q_{refill}(t^{0-}) = 0$ and ECW(t)=ECW(0) and BV(t)=BV(0), thus $$Q_{refill}(t^{0-}) = 0 = [ECW(0) - BV(0) \cdot k_1(0)] \cdot k_r \qquad \text{Eq. 19}$$

Therefore $$k_1(0) = \frac{ECW(0)}{BV(0)} = \frac{ECW_{Norm} + OH(0)}{BV(0)} \qquad \text{Eq. 20}$$

Introducing the relative blood volume, RBV(t) the initial absolute blood volume, $BV_0$, the normally hydrated extracellular volume $ECV_{Norm}$, and the overhydration OH(t) then Eq. 18 can be rewritten:

$$Q_{refill}(t) = [ECW_{Norm} + OH(t) - RBV(t) \cdot (ECW_{Norm} + OH(0))] \cdot k_r \qquad \text{Eq. 21}$$

Rearranging Eq. 17 for $Q_{refill}(t)$ $$Q_{refill}(t) = \dot{R} \cdot BV_0 + Q_{UFR}(t) \qquad \text{Eq. 22}$$

During treatment, the following relationship always holds true:

$$OH(t) = OH(0) - V_u(t) \qquad \text{Eq. 23}$$

$V_u(t)$ being the ultrafiltration volume at time t during treatment.

Equating Eq. 21 with Eq. 22 leads to $$\dot{R} \cdot BV_{Norm} + \dot{R} \cdot f_n(OH(0)) + Q_{UFR}(t) = [ECW_{Norm} + OH(0) - V_u(t) - RBV(t) \cdot (ECW_{Norm} + OH(0))] \cdot k_r \qquad \text{Eq. 24}$$

Where the function $f_n$ is defined as follows:

$$f_n(OH(0)) = f_1 \,\forall\, OH(0) < 0 \text{ or } f_n = f_2 \,\forall\, OH(0) \geq 0 \qquad \text{Eq. 25}$$

As a cross check, at initial conditions in steady state ($t=0^-$), $d(RBV)/dt=0$, RBV(0)=1, Qufr(0)=0, Vu(0)=0 and both left and right sides of Eq. 24 equate to 0 as expected. Also a special case exists at $t=0^+$ (the start of ultrafiltration) whereby Eq. 24 reduces to $$\dot{R} \cdot BV_{Norm} + \dot{R} \cdot f_n(OH(0)) + Q_{UFR}(0^+) = 0 \qquad \text{Eq. 26}$$

Figure 9:
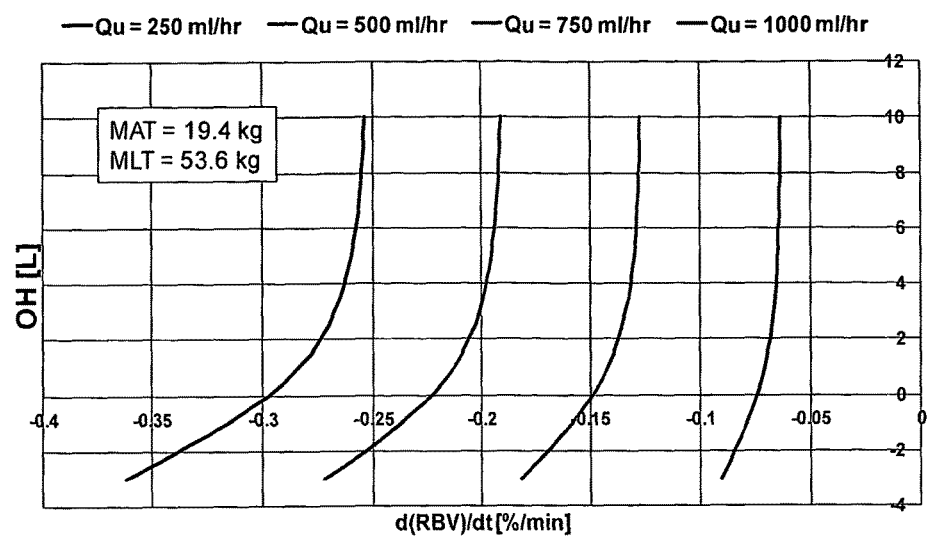
FIG. 9 depicts a dependency between overhydration and relative blood volume variation rate

Using Eq. 26, OH(0) can be plotted against $d(RBV)/dt$ for different values of ultrafiltration rate $Q_{UFR}(0^+)$ which is shown in FIG. 9.

I.e. in particular FIG. 9 depicts a relationship between OH and $d(RBV)/dt$ for different values of Qufr(0) in a reference subject with MAT=19.4 kg and MLT=53.6 kg In FIG. 9, the leftmost curve relates to an ultrafiltration rate of 1000 ml/hr, the left medium curve relates to 750 ml/hr ultrafiltration rate, the right medium curve relates to 500 ml/hr ultrafiltration rate and the rightmost curve relates to an ultrafiltration rate of 250 ml/hr.

When the vascular space is saturated (maximum blood volume) Eq. 26 is further reduced and when rearranged for the maximum rate of change of RBV, $d(RBV)/dt\_max$ leads to:

$$\dot{R}_{max} = \frac{-Q_{ufr}}{BV_{Norm} + \beta \cdot \delta V_{i\_Gel\_max}} = \frac{-Q_{ufr}}{BV_{max}} \,\forall\, OH \geq 0 \qquad \text{Eq. 27}$$

In Equation 27 the index max indicates respective maximum values at the beginning of the treatment.

In other words, the maximum rate of change in relative blood volume is dependent on the ultrafiltration rate and the maximum blood volume. This corresponds to the asymptotes implied in I.e. in particular FIG. 9. It is also apparent that the upper limit of OH that can be determined is limited to ca. 3 to 7 liters (depending on the UFR), due to the high sensitivity to $d(RBV)/dt$. With a higher ultrafiltration rate the accuracy in calculating OH increases. In a patient with a low UF volume for example, a UF profile which increases UFR at the start of treatment, stepping down to lower values as treatment progresses (See FIG. 10) will help to increase OH calculation accuracy and extend the upper OH range that can be determined.

Figure 10:
FIG. 10 depicts a stepped ultrafiltration profile

I.e. as depicted in FIG. 10 a stepped UF profile is proposed to allow UFR to be increased at the start of dialysis.

Eq. 26 Can be solved for OH(0) yielding $$OH(0) = \frac{-1}{\lambda} \cdot \ln\left( \frac{Q_{ufr}(0^+) + \dot{R}(0^+) \cdot BV_{Norm}}{\dot{R}(0^+) \cdot \beta \cdot \delta V_{i\_Gel\_max}} \right) \,\forall\, OH \geq 0 \qquad \text{Eq. 28}$$

and $$OH(0) = \frac{-Q_{ufr}(0^+) - \dot{R} \cdot BV_{Norm}}{\dot{R} \cdot \alpha \cdot \beta} \,\forall\, OH < 0 \qquad \text{Eq. 29}$$

Eq. 26 has obvious utility since the refilling constant $k_r$ is not involved. Furthermore Eq. 26 could be primed with a known value of OH(0) from the BCM and solved for the product $\beta \cdot \delta V_{i\_Gel\_max}$ for some further optimization.

Eq. 24 contains two unknowns, namely the initial overhydration and the refill constant $k_r$. Using the BCM to obtain OH(0) as a standard, then $k_r$ can be determined for an individual patient as a calibration. If $k_r$ is assumed constant from treatment to treatment Eq. 24 can be solved for OH thus providing a calibrated method for determining the overhydration OH. Eq. 24 is transcendental and therefore needs to be solved numerically. Some algorithms (such as Newton-Raphson) could be derived to speed up a solution but since the likely range of OH is usually known, it would be just as easy to step through values of OH at 0.1 L increments.

Another option would be to overdetermine Eq. 24, using values of RBV(t), d(RBV)/dt, Vu(t) and Qufr(t) at different time intervals allowing OH(0) and $k_r$ to be calculated. While OH(0) is obviously single valued, $k_r$ could be obtained during different stages of the treatment which may be of value if $k_r$ changes over time due to treatment circumstances e.g. heat loss effects, vasoconstriction etc.

The invention claimed is:

1. An apparatus comprising:
a digital signal processor having a memory;
a first determination unit operative with said digital signal processor and configured to determine a normalized change of a blood parameter ($\Delta$RBV) of an individual during a treatment session;
a second determination unit operative with said digital signal processor and configured to determine a fluid status of the individual; and
a calibration unit operative with said digital signal processor and adapted to calibrate the determined normalized change of the blood parameter ($\Delta$RBV) provided by the first determination unit based on the fluid status provided by the second determination unit;
the apparatus being configured to perform a quantitative determination of the fluid status or a change in the fluid status by:
determining, using at least the first determination unit, a first change of the blood parameter ($\Delta$RBV) of the individual during a first treatment session normalized by at least one of ultrafiltration volume and ultrafiltration rate of the first treatment session;
determining, using at least the second determination unit, a first fluid status of the individual;
calibrating, using at least the calibration unit, the determined normalized first change of the blood parameter ($\Delta$RBV) based on the first fluid status;
determining, using at least the first determination unit, a further change of the blood parameter during at least one further treatment session normalized by at least one of ultrafiltration volume and ultrafiltration rate of the at least one further treatment session;
deriving, using at least the second determination unit, the fluid status or a change in the fluid status from the normalized further change of the blood parameter; and
using the derived fluid status or the change in fluid status as determined using the apparatus to detect fluid overload and to mitigate health risks to the individual related to fluid overload.

2. The apparatus, according to claim 1, wherein the calibration unit is further adapted to determine a second normalized change of the blood parameter ($\Delta$RBV) and a second fluid status during a second treatment session, wherein the calibration of the change of the blood parameter ($\Delta$RBV) is based on the normalized first and second changes of the blood parameter ($\Delta$RBV) and on the first and second fluid status.

3. The apparatus according to claim 1, wherein the blood parameter includes a concentration of hemoglobin in the blood.

4. The apparatus according to claim 1, wherein the treatment session is a dialysis and/or ultrafiltration treatment session.

5. The apparatus according to claim 1, wherein the apparatus approximates the change of the blood parameter ($\Delta$RBV) using a polynomial regression.

6. The apparatus according to claim 5, wherein the calibration unit is configured to determine at least one constant C and/or a coefficient k of a polynomial.

7. The apparatus according to claim 1, wherein the fluid status is determined by an assessment of a blood composition of the individual.

8. The apparatus according to claim 1, in combination with a database, wherein the combination is configured to operate such that a first and/or second fluid status, an updated fluid status, a normal fluid status, a normohydration weight or any other data gained throughout a treatment session is transferred to the database via a data connection.

9. The combination according to claim 8, wherein the database is operated at a central server.

10. The combination according to claim 8 wherein the transferred data is processed such that statistics and/or conclusions for the treatment of the individual and/or a specific group of individuals with comparable body parameters, may be derived.

11. The apparatus according to claim 1, wherein the apparatus is adapted to use the fluid status and/or any other data gained throughout at least one of the treatment sessions to determine a dosage of a medicament selected from the group consisting of EPO, sodium and iron preparations.

12. The apparatus according to claim 1, wherein the apparatus is configured to determine the fluid status by bioimpedance spectroscopy of the individual.

13. Computer-readable non-transitory storage medium comprising instructions to be executed on an apparatus, said apparatus including a memory, a digital signal processor, a first determination unit configured to determine a normalized change of a blood parameter ($\Delta$RBV) of an individual during a treatment session, a second determination unit to determine a fluid status of the individual, and a calibration unit to calibrate the determined normalized change of the blood parameter ($\Delta$RBV) based on the fluid status, the instructions configured for controlling the apparatus to perform a quantitative determination of the fluid status or a change in the fluid status by determining a first change of the blood parameter ($\Delta$RBV) of the individual during a first treatment session normalized by at least one of ultrafiltration volume and ultrafiltration rate of the first treatment session using at least the first determination unit, to determine a first fluid status of the individual using at least the second determination unit, to calibrate the determined normalized first change of the blood parameter ($\Delta$RBV) based on the first fluid status using at least the calibration unit, to determine a further change of the blood parameter during at least one further treatment session normalized by at least one of ultrafiltration volume and ultrafiltration rate of the at least one further treatment session using at least the first determination unit, to derive the fluid status or a change in the fluid status from the normalized further change of the blood parameter using at least the second determination unit, and to use the derived fluid status or the change in fluid status to detect fluid overload and to mitigate health risks to the individual related to fluid overload.

* * * * *